(12) United States Patent
Verleur (10) Patent No.: US 10,874,141 B2
(45) Date of Patent: Dec. 29, 2020

(54) VAPORIZER

(71) Applicant: VMR Products, LLC, Miami, FL (US)

(72) Inventor: Jan Andries Verleur, Miami Beach, FL (US)

(73) Assignee: VMR Products, LLC, Miami, FL (US)

( * ) Notice: Subject to any disclaimer, the term of this patent is extended or adjusted under 35 U.S.C. 154(b) by 0 days.

(21) Appl. No.: 14/913,340

(22) PCT Filed: Aug. 20, 2014

(86) PCT No.: PCT/US2014/051900
§ 371 (c)(1),
(2) Date: Feb. 19, 2016

(87) PCT Pub. No.: WO2015/026948
PCT Pub. Date: Feb. 26, 2015

(65) Prior Publication Data
US 2016/0198767 A1    Jul. 14, 2016

Related U.S. Application Data

(60) Provisional application No. 61/867,790, filed on Aug. 20, 2013.

(51) Int. Cl.
*H05B 1/02* (2006.01)
*A61M 15/00* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ... A24F 47/008; H05B 1/0202; H05B 6/6458; H01S 2302/00; H01S 3/06708;
(Continued)

(56) References Cited

U.S. PATENT DOCUMENTS

| | | |
|---|---|---|
| 4,947,874 A | 8/1990 | Brooks et al. |
| 4,947,875 A | 8/1990 | Brooks et al. |

(Continued)

FOREIGN PATENT DOCUMENTS

| | | |
|---|---|---|
| CA | 2641869 A1 | 5/2010 |
| CA | 2846286 A1 | 4/2013 |

(Continued)

OTHER PUBLICATIONS https://nehagirme.wordpress.com/2011/10/22/design-of-capacitive-level-sensor/.*

(Continued)

*Primary Examiner* — Michael A LaFlame, Jr.
(74) *Attorney, Agent, or Firm* — Mintz Levin Cohn Ferris Glovsky and Popeo, P.C.

(57) ABSTRACT

A vaporizer may include a battery housing and a cartomizer connectable to the battery housing. A battery may be housed within the battery housing. The cartomizer may have a cartomizer body dimensioned to hold a vaporizable substance. The cartomizer may also include a heating element to heat the vaporizable substance. A cutoff device may be connectable to the heating element to disrupt the heating element.

24 Claims, 6 Drawing Sheets

(51) Int. Cl.
 *A24F 47/00* (2020.01)
 *A61M 11/04* (2006.01)
 *A61M 15/06* (2006.01)
 *A61M 16/00* (2006.01)

(52) U.S. Cl.
 CPC ......... *H05B 1/0202* (2013.01); *A61M 15/008* (2014.02); *A61M 15/0081* (2014.02); *A61M 2016/0024* (2013.01); *A61M 2016/0027* (2013.01); *A61M 2205/3368* (2013.01); *A61M 2205/3386* (2013.01); *A61M 2205/50* (2013.01); *A61M 2205/583* (2013.01); *A61M 2205/8206* (2013.01)

(58) Field of Classification Search
 CPC ............ H01S 3/06733; H01S 3/06754; H01S 3/08059; H01S 3/094003; H01S 3/0941; H01S 3/105; H01S 3/1053; H01S 3/1055; H01S 3/1603; H01S 3/1608; H01S 3/161; H01S 3/302; H01S 5/0028; H01S 5/02284; H01S 5/06; H01S 5/0607; H01S 5/0612; H01S 5/06804; H01S 5/06837; H01S 5/10; H01S 5/18366; H01S 5/18369; H01S 5/4012; A61M 15/00
 USPC ....... 392/386, 390, 391, 394, 395–398, 407, 392/409, 410, 441, 465, 476–477; 219/544, 520, 687, 401, 413, 506, 398, 219/400, 688; 131/328, 329, 273, 270, 131/271, 194; 122/406.4, 14.2, 448.4; 73/304 C; 99/330, 331, 324, 357, 474, 99/403, 467, 480; 128/202.21
 See application file for complete search history.

(56) References Cited

U.S. PATENT DOCUMENTS

| | | | |
|---|---|---|---|
| 5,060,671 A | 10/1991 | Counts et al. | |
| 5,144,962 A | 9/1992 | Counts et al. | |
| 5,175,791 A | 12/1992 | Muderlak et al. | |
| 5,269,327 A | 12/1993 | Counts et al. | |
| 6,155,268 A | 12/2000 | Takeuchi | |
| 6,407,371 B1 | 6/2002 | Toya et al. | |
| 6,766,220 B2 | 7/2004 | McRae et al. | |
| 7,143,766 B2 | 12/2006 | Schuster et al. | |
| 7,400,940 B2 | 7/2008 | McRae et al. | |
| 8,550,069 B2* | 10/2013 | Alelov | A61M 11/005 128/202.21 |
| 8,910,640 B2* | 12/2014 | Sears | A24F 47/008 128/202.21 |
| 9,016,274 B1 | 4/2015 | White | |
| 9,240,300 B2* | 1/2016 | Xu | H01C 1/14 |
| 9,247,773 B2 | 2/2016 | Memari et al. | |
| 9,423,152 B2* | 8/2016 | Ampolini | A24F 47/008 |
| 9,427,022 B2 | 8/2016 | Levin et al. | |
| 9,459,021 B2 | 10/2016 | Greim et al. | |
| 9,480,286 B2 | 11/2016 | Liu | |
| 9,596,884 B2 | 3/2017 | Liu | |
| 9,596,885 B2 | 3/2017 | Liu | |
| 9,668,522 B2 | 6/2017 | Memari et al. | |
| 9,682,204 B2 | 6/2017 | Matsumoto et al. | |
| 9,730,471 B2 | 8/2017 | Li et al. | |
| 9,781,953 B2 | 10/2017 | Verleur et al. | |
| 9,802,011 B2 | 10/2017 | Davidson et al. | |
| 9,814,263 B2 | 11/2017 | Cochand et al. | |
| 9,999,250 B2 | 6/2018 | Minskoff et al. | |
| 10,064,434 B2 | 9/2018 | Zitzke et al. | |
| 10,085,481 B2 | 10/2018 | Verleur et al. | |
| 10,131,532 B2 | 11/2018 | Murison et al. | |
| 2007/0102013 A1 | 5/2007 | Adams et al. | |
| 2010/0031968 A1 | 2/2010 | Sheikh et al. | |
| 2010/0164733 A1* | 7/2010 | Ales | A61F 13/42 340/604 |
| 2012/0234821 A1 | 9/2012 | Shimizu | |
| 2012/0279512 A1 | 11/2012 | Hon | |
| 2012/0318882 A1* | 12/2012 | Abehasera | A61M 11/041 239/1 |
| 2012/0325227 A1 | 12/2012 | Robinson et al. | |
| 2013/0081642 A1 | 4/2013 | Safari | |
| 2013/0180315 A1* | 7/2013 | Snow | G05D 22/02 73/29.02 |
| 2013/0199528 A1 | 8/2013 | Goodman et al. | |
| 2013/0306084 A1 | 11/2013 | Flick | |
| 2013/0319435 A1 | 12/2013 | Flick | |
| 2014/0062417 A1 | 3/2014 | Li et al. | |
| 2014/0123989 A1 | 5/2014 | LaMothe | |
| 2014/0150785 A1 | 6/2014 | Malik et al. | |
| 2014/0178461 A1 | 6/2014 | Rigas | |
| 2014/0238424 A1 | 8/2014 | Macko et al. | |
| 2014/0253144 A1 | 9/2014 | Novak, III et al. | |
| 2014/0261491 A1 | 9/2014 | Hawes | |
| 2014/0270727 A1* | 9/2014 | Ampolini | A24F 47/008 392/387 |
| 2014/0283856 A1 | 9/2014 | Xiang | |
| 2014/0305454 A1* | 10/2014 | Rinker | A24F 47/008 131/329 |
| 2014/0332017 A1 | 11/2014 | Liu | |
| 2014/0338685 A1 | 11/2014 | Amir | |
| 2014/0366898 A1* | 12/2014 | Monsees | A24F 47/008 131/329 |
| 2014/0373857 A1 | 12/2014 | Steinberg | |
| 2015/0013692 A1 | 1/2015 | Liu | |
| 2015/0040925 A1 | 2/2015 | Saleem et al. | |
| 2015/0047662 A1 | 2/2015 | Hopps | |
| 2015/0075545 A1 | 3/2015 | Xiang | |
| 2015/0101623 A1 | 4/2015 | Liu | |
| 2015/0107609 A1 | 4/2015 | Liu | |
| 2015/0114410 A1 | 4/2015 | Doster | |
| 2015/0122274 A1 | 5/2015 | Cohen et al. | |
| 2015/0128967 A1 | 5/2015 | Robinson et al. | |
| 2015/0181945 A1 | 7/2015 | Tremblay | |
| 2015/0223521 A1 | 8/2015 | Menting et al. | |
| 2015/0245654 A1 | 9/2015 | Memari et al. | |
| 2015/0245655 A1 | 9/2015 | Memari et al. | |
| 2015/0245657 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0258289 A1 | 9/2015 | Henry, Jr. et al. | |
| 2015/0282525 A1 | 10/2015 | Plojoux et al. | |
| 2015/0305406 A1 | 10/2015 | Li et al. | |
| 2015/0305409 A1 | 10/2015 | Verleur et al. | |
| 2016/0020048 A1 | 1/2016 | Ware | |
| 2016/0044963 A1 | 2/2016 | Saleem | |
| 2016/0081394 A1 | 3/2016 | Alarcon et al. | |
| 2016/0150824 A1 | 6/2016 | Memari et al. | |
| 2016/0198767 A1 | 7/2016 | Verleur | |
| 2016/0278436 A1 | 9/2016 | Verleur et al. | |
| 2016/0374398 A1 | 12/2016 | Amir | |
| 2017/0042242 A1 | 2/2017 | Hon | |
| 2017/0099880 A1 | 4/2017 | Hawes | |
| 2017/0188634 A1 | 7/2017 | Plojoux et al. | |
| 2017/0202267 A1 | 7/2017 | Liu | |
| 2017/0207499 A1* | 7/2017 | Leadley | A24F 47/008 |
| 2017/0246407 A1 | 8/2017 | Matsumoto et al. | |
| 2017/0295848 A1 | 10/2017 | LaMothe | |
| 2018/0368481 A1 | 12/2018 | Verleur et al. | |
| 2019/0069605 A1 | 3/2019 | Verleur et al. | |
| 2019/0082740 A1 | 3/2019 | Verleur et al. | |

FOREIGN PATENT DOCUMENTS

| | | |
|---|---|---|
| CA | 2622481 C | 7/2015 |
| CN | 201104488 Y | 8/2008 |
| CN | 203166461 U | 8/2013 |
| CN | 203851801 U | 10/2014 |
| CN | 203952421 U | 11/2014 |
| EP | 0 358 002 A2 | 3/1990 |
| EP | 0358114 A2 | 3/1990 |
| EP | 0 430 559 A2 | 6/1991 |

(56) References Cited

FOREIGN PATENT DOCUMENTS

| | | |
|---|---|---|
| EP | 2 468 118 A1 | 6/2012 |
| GB | 1025630 A | 4/1966 |
| KR | 101363964 B1 | 2/2014 |
| KR | 101682319 B1 | 12/2016 |
| WO | WO-0005976 A1 | 2/2000 |
| WO | WO-2010118644 A1 | 10/2010 |
| WO | WO-2012027350 A2 | 3/2012 |
| WO | WO-2013147492 A1 | 10/2013 |
| WO | WO-2014134781 A1 | 9/2014 |
| WO | WO-2014146270 A1 | 9/2014 |

OTHER PUBLICATIONS

International Search Report issued in related International Application No. PCT/US2014/051900, US International Searching Authority, dated Dec. 18, 2014.
Written Opinion of the International Searching Authority issued in related International Application No. PCT/US2014/051900, US International Searching Authority, dated Dec. 18, 2014.
Extended European Search Report for corresponding European Pat. Appln. No. EP 14837480.4, completed Feb. 28, 2017, dated Mar. 8, 2017.

* cited by examiner

VAPORIZER

CROSS REFERENCE TO RELATED APPLICATIONS

This application is a national stage application of International Application No. PCT/US2014/051900, filed Aug. 20, 2014, which claims the benefit of U.S. Provisional Application No. 61/867,790, filed Aug. 20, 2013, the disclosure of which is hereby incorporated herein by reference in its entirety.

FIELD OF THE DISCLOSURE

This disclosure relates to the field of vaporizers, which may also be referred to as electronic cigarettes.

BACKGROUND

Electronic cigarettes have recently emerged as a new product for providing nicotine through a smokeless inhalation process. Typically, implementations consist of a power supply (typically a battery) and an atomizing device. In reusable electronic cigarettes the two items are separated into a battery and a cartomizer, to allow the disposal and replacement of a nicotine containing fluid cartomizer while preserving the more costly battery and associated circuitry (microcontroller, switch, indicating LED, etc.) for additional use. In disposable electronic cigarettes, the two items are combined to integrate the functions into one unit that is discarded after either the battery energy or the nicotine containing liquid is exhausted.

The electronic cigarette liquid used to vaporize ingredients such as nicotine is generally a solution of propylene glycol (PG), vegetable glycerin (VG), or polyethylene glycol 400 (PEG400), as well as their mixtures to which a flavor and/or nicotine has been added. The solution is often sold in a bottle (for refilling by the user) or in disposable cartridges or cartomizers. Many different flavors are incorporated into these liquids, including those that resemble the taste of regular tobacco, menthol, vanilla, coffee, cola and/or various fruits. Various nicotine concentrations are also available, and nicotine-free solutions are also common.

BRIEF SUMMARY OF THE DISCLOSURE

The following presents a simplified summary of the disclosure in order to provide a basic understanding of some aspects of various embodiments disclosed herein. This summary is not an extensive overview of the disclosure. It is intended to neither identify key or critical elements of the disclosed embodiments nor delineate the scope of those embodiments. Its sole purpose is to present some concepts of the invention in a simplified form as a prelude to the more detailed description that is presented later.

One embodiment of a vaporizer, in accordance with the disclosure, may include a battery housing. The vaporizer may also include a battery housed within the battery housing. The vaporizer may further include a cartomizer connectable to the battery housing, the cartomizer including a cartomizer body dimensioned to hold a vaporizable substance and a heating element operable to heat the vaporizable substance. The vaporizer may also include a cutoff device connectable to the heating element operable to disrupt the heating element.

DETAILED DESCRIPTION OF THE DISCLOSURE

The following detailed description and the appended drawings describe and illustrate various embodiments of the instant disclosure solely for the purpose of enabling one of ordinary skill in the relevant art to make and use such embodiments. As such, the detailed description and illustration of these embodiments are purely representative and illustrative in nature and are in no way intended to limit the scope of the invention, or its protection, in any manner. It should also be understood that the drawings are not to scale and in certain instances details have been omitted, which are not necessary for an understanding of the present disclosure, such as conventional details of fabrication and assembly.

One embodiment of a vaporizer, in accordance with the disclosure, may include a battery housing. The vaporizer may also include a battery housed within the battery housing. The vaporizer may further include a cartomizer connectable to the battery housing, the cartomizer including a cartomizer body dimensioned to hold a vaporizable substance and a heating element operable to heat the vaporizable substance. The vaporizer may also include a cutoff device connectable to the heating element operable to disrupt the heating element.

In some embodiments, the cutoff device may be a fuse connectable to the battery and the heating element and operable to melt at a predetermined temperature. In other embodiments, the cutoff device may be a switch operable to interrupt a current flow to the heating element. The switch may be housed within the cartomizer. The switch may also be housed within the battery housing. The cutoff device may further include a temperature sensor connectable to the switch. In some embodiments the cutoff device may further include a fluid level sensor connectable to the switch. The cutoff device may also include a processor operable to determine a number of times the cartomizer is activated through a user's inhalation.

Additional embodiments of the vaporizer may include an indicator operable to signal a user when the heating element is disrupted. The vaporizer may also include a first threaded connector arranged on the battery housing and a second threaded connector arranged on the cartomizer body and connectable to the first threaded connector. The vaporizer may further include a pressure switch. In some embodiments the vaporizer may include a printed circuit board connectable to the battery. The printed circuit board is arranged in the battery housing. The printed circuit board may also be arranged in the cartomizer body.

Figure 1:
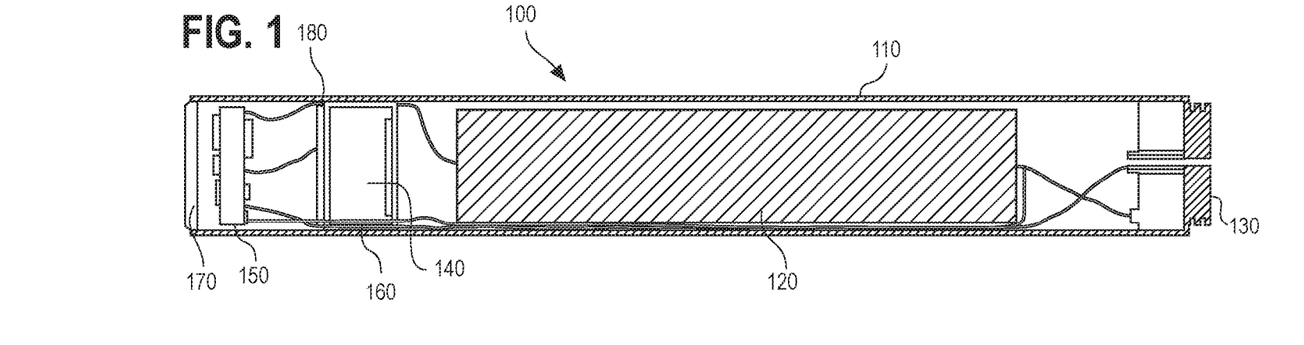
FIG. 1 illustrates an embodiment of a battery housing of a vaporizer in accordance with the disclosure.

With reference to FIG. 1, an embodiment of a battery housing 100 for a vaporizer may include a tube 110, a battery 120, an output connector 130, a pressure switch 140, a printed circuit board 150, a rubber or plastic grommet 160, a translucent plastic cover 170, and an insulating plastic 180.

Figure 3:
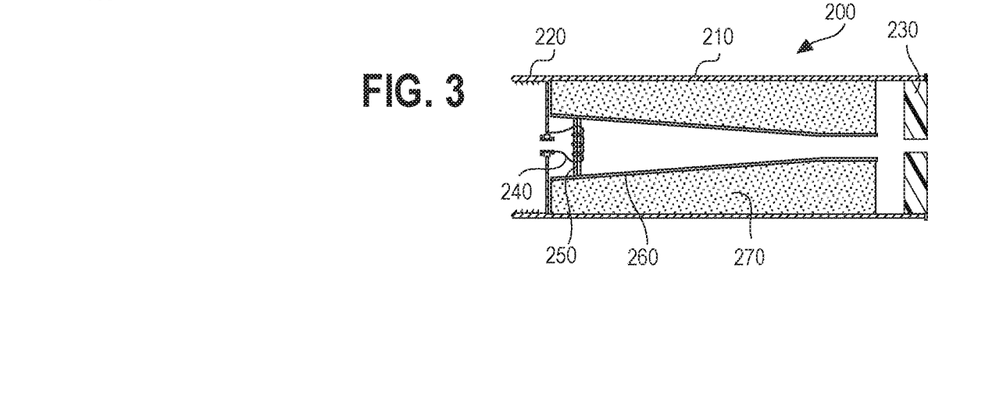
FIG. 3 illustrates an embodiment of a cartomizer of a vaporizer in accordance with the disclosure.

The tube 110 may be constructed from aluminum or another suitable material, and may be manufactured in a variety of diameters. The battery 120 may be, for example, a lithium battery, or another type of battery known or to be developed to those of ordinary skill in the art. Various battery models and sizes may be used depending upon desired size and battery capacity. In some embodiments, the battery 120 may be permanently installed and not removable by a user. The output connector 130 may be male threaded, for instance a KR808D1 threading, and may be a milled assembly that is friction fitted into the tube 110. An adhesive may be used to secure the output connector 130 to the tube 110. The pressure switch 140 may be one of several types of known or to be developed pressure switches depending on the manufacturer. The pressure switch 140 may be activated by pressure differential created by a user inhaling on a cartomizer 200 (as illustrated in FIG. 3), which may be connected to the battery housing 100. Airflow may be through a center aperture in the cartomizer 200 and the output connector 130. In some cases there is an air hole in the output connector 130 that allows some of the air to come from outside the battery 120, as only a small pressure differential may be required to activate the battery 120.

The Printed Circuit Board (PCB) 150 may include, for example, a light emitting diode (LED), a microcontroller, at least one capacitor, and at least one resistor. The PCB 150 may operate to control voltage from the battery 120 provided to the output connector 130. The PCB 150 may also operate to control the LED light (such as blinking after use and upon initiation of charging of battery 120). During manufacturing, the PCB 150 may be mounted lengthwise in the tube 110 (that is rotated normal to the orientation illustrated in FIG. 1). The grommet 160 may be rubber, plastic, or another suitable material for sealing the pressure switch 140 to tube 110 in order to prevent air leaking around the switch 140. The cover 170 may be translucent and plastic may be provided over the LED light to permit light to show through the cover 170. One or more openings, holes, or gaps may be provided in the cover 170 to permit a small amount of airflow in order to permit activation of the pressure switch 140 upon inhalation by the user. Insulating plastic 180 may be provided to prevent the PCB 150 and the wires from shorting the pressure switch 140.

Figure 2:
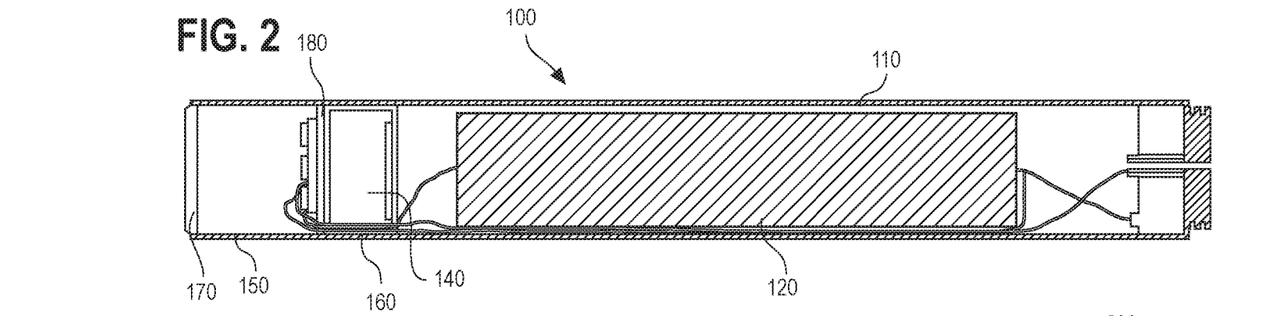
FIG. 2 illustrates another embodiment of a battery housing of a vaporizer in accordance with the disclosure.

The illustrated embodiment in FIG. 1 is an automatic battery where inhalation automatically activates the battery 120. A manual version of a cigarette battery is further contemplated within the disclosure by replacing the pressure switch 140 with a manual switch which may be mounted on the tube 110 proximate to the output connector 130. FIG. 2 illustrates an embodiment where pressure switch 140 and PCB 150 are manufactured into a single assembly.

FIG. 3 illustrates an embodiment of a cartomizer 200 for a vaporizer, which may include a cartomizer body 210, a mating connector 220, a mouth piece 230, a heating element 240, fiberglass fibers 250, a heat insulting tube 260, and fiber batting 270.

The cartomizer body 210 may be a tube and may be constructed from aluminum or another suitable material. The cartomizer body 210 may be dimensioned to hold a vaporizable liquid and may be manufactured in a variety of diameters. The cartomizer body 210 may have a diameter substantially matching the diameter of tube 110. The mating connector 220 may have a female threading matching the output connector 130, for instance a KR808D1 female threading. An adhesive may be used to secure the mating connector 220 to the cartomizer body 210. The mouth piece 230 may be constructed from plastic or another suitable material and may have a hole to permit airflow to the user for inhalation. The heating element may be a wire and may be manufactured from a nichrome filament or other suitable material. The heating element 240 may be connected to the mating connector 220 to allow activation of the heating element 240 by the battery 120. Various known or to be developed methods for attaching the heating element 240 are contemplated within the disclosure. Fiberglass fibers 250 may be associated with the heating element 240 in that the fiberglass fibers 250 may be constructed as a "rope" wound about heating element 240. Each individual heating element 240 may be cut from the larger piece of "rope" during manufacturing. The fiberglass fibers 250 may provide structural support for the heating element 240 and prevent or resist motion due to, for instance, dropping of the electronic cigarette, which may result in an electrical short. The heat insulating tube 260 may provide a path for airflow and prevent the fiber batting 270 from directly contacting the heating element 240. The fiber batting 270, which may also be referred to as the fluid reservoir, may include poly fiber acting as a sponge to hold a nicotine containing fluid or other vaporizable fluid. The reservoir 270 may thus prevent the vaporizable fluid from leaking out of the cartomizer 200. In some embodiments, plastic runner washers are utilized, having various shapes and configurations, to at least partially prevent the vaporizable fluid from leaking.

A charger assembly (not illustrated) may be included with a vaporizer in order to recharge the battery 120. The charger assembly may contain a mating connector similar to the mating connector 220 to allow an electrical connection to the battery holder. The charge may provide between 4-5 volts at approximately 200 mA to charge the battery 120. During charging operation the microcontroller of the PCB 150 may inhibit the voltage output and may blink the LED light a set number of times, three times for instance, to indicate the start of the charging cycle. A red and green LED on the charger assembly may indicate either charging (red) or charged (green) status. Once the battery 120 is charged, a user may disconnect the battery housing from the charger and connect the battery housing 100 to the cartomizer 200. Cartomizers with vaporizable fluid of various flavors and strengths of nicotine may be made available. Once the cartomizer 200 is attached to the battery housing 100, the user may inhale directly on the cartomizer 200 in the case of an automatic battery housing, as illustrated, or the user may press the manual switch on a manual battery housing. The heating element 240 may heat the vaporizable fluid, upon activation, which vaporizes thereby creating the smoke-like vapor infused with nicotine and other flavorings.

The airflow allows multiple paths from outside the battery housing 100 to the user. One air flow path may be through the cover 170, which allows pressure switch 140 to activate as one side is exposed to normal atmospheric pressure while the opposing side is exposed to negative pressure from suction of the user. Another airflow path may be through holes in the connectors' 130, 220 threads. As the air goes through the cartomizer 200 it may mix with the fluid vapor and may be inhalable by the user.

Figure 4:
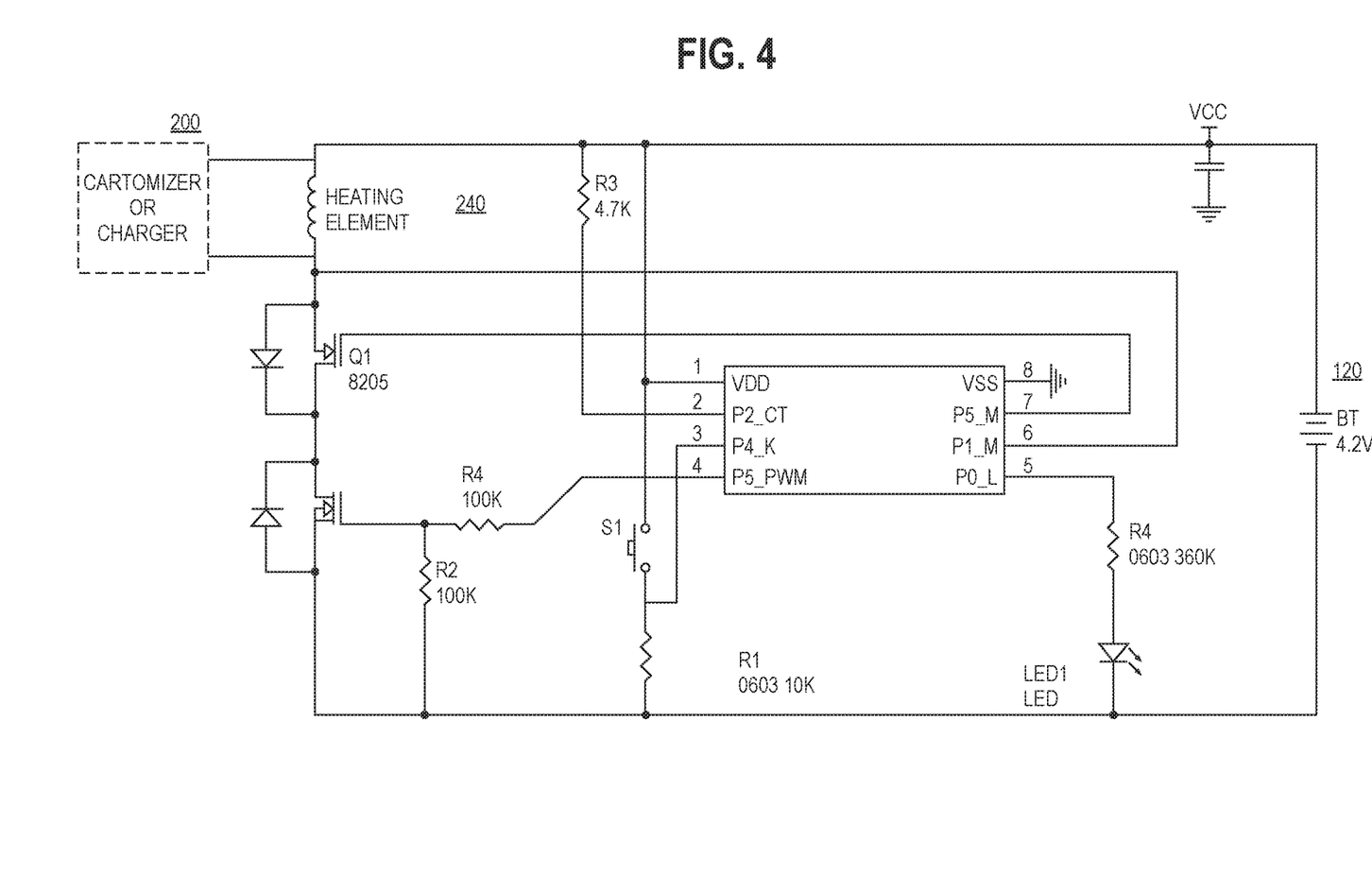
FIG. 4 illustrates an embodiment of an electrical schematic as utilized in controlling a vaporizer in accordance with the disclosure.

An embodiment of an electrical schematic diagram for the PCB 150 and other elements of a vaporizer is shown and described in FIG. 4.

Figure 5:
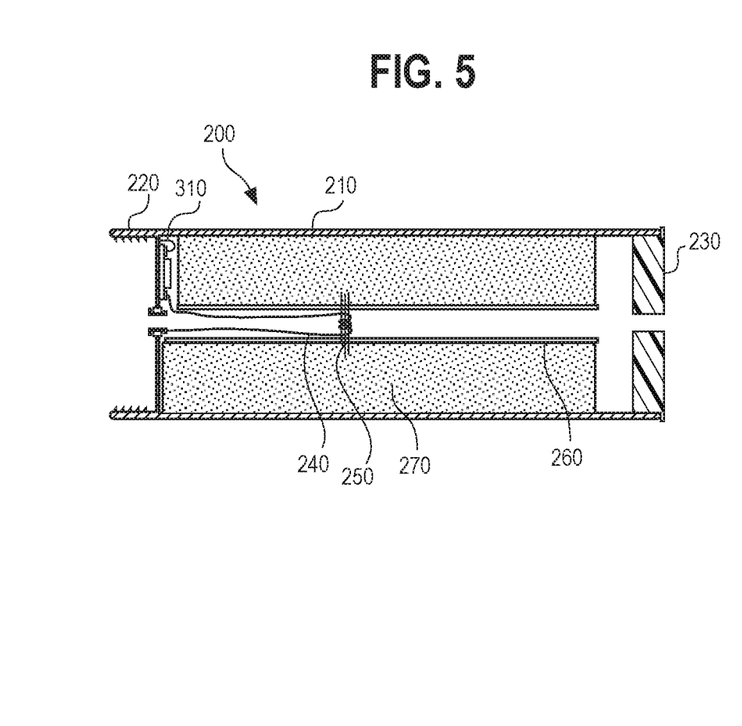
FIG. 5 illustrates another embodiment of a cartomizer of a vaporizer in accordance with the disclosure.

FIGS. 5 through 10 illustrate embodiments which may include a cutoff device which may detect and react to a rapid rise in temperature associated with the exhaustion of the vaporizable liquid. As illustrated in FIG. 5, the cutoff device can take the form of a fusible link 310 that separates or melts above a predetermined temperature to open the circuit and prevent the delivery of current from the battery 120 to the heating element 240. The fusible link 310 can be in the form of a fuse like device wherein the electrical current that flows to the heating element 240 passes through the fuse. If the temperature exceeds a predetermined level the fuse may be designed to melt or open. The location of the fusible link 310 may be changed to allow more or less exposure to the heat generated by the heating element 240 and adjust the level of vaporizable fluid remaining when the fusible link 310 opens. In some embodiments, additional wire connections may be provided so that the heating element 240 does not attach directly to the fusible link 310 to prevent the heating element 240 from tripping the fuse in normal use.

Figure 6:
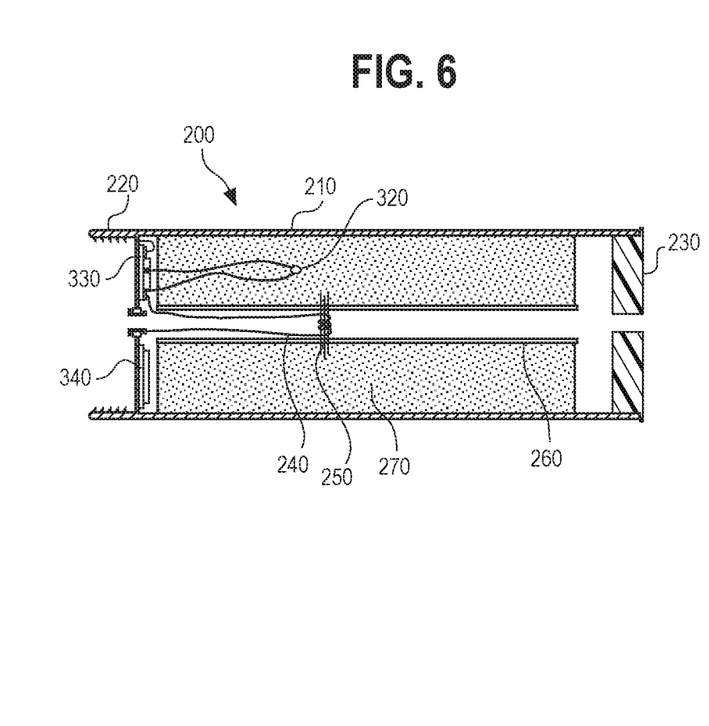
FIG. 6 illustrates another embodiment of a cartomizer of a vaporizer in accordance with the disclosure.
Figure 7:
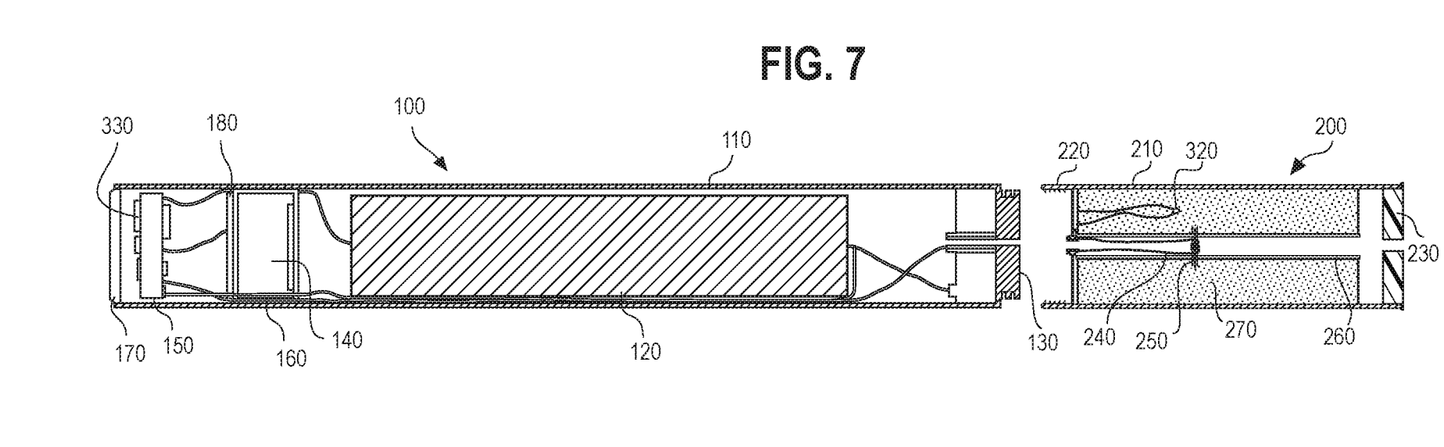
FIG. 7 illustrates an exploded view of embodiment of a vaporizer including a battery housing and a cartomizer in accordance with the disclosure.

Another embodiment including a temperature sensor 320 and associated circuitry is contemplated within the disclosure as described in reference to FIGS. 6 and 7. In the embodiment illustrated in FIG. 6, the sensor 320 and associated circuitry may be contained in the cartomizer 200. The temperature sensor 320, such as a thermocouple, thermistor, RTD, or other known or to be developed temperature sensors, may be placed inside the cartomizer 200 in proximity to the heating element 240. The associated circuitry may be capable of amplifying and determining if the temperature is above some predetermined level, as well as a switch 330, such as a Power FET, to interrupt flow of current to the heating element 240, is installed upon a small PCB 340, also contained in the cartomizer 200.

Another embodiment may include temperature sensor 320 in the cartomizer 200 and the associated circuitry in the battery section, as illustrated in FIG. 7. The temperature sensor 320 may be placed inside the cartomizer 200 in close proximity to the heating element 240. The associated circuitry and switch 330 may be added to the PCB 150 of the battery housing 100. The output of this circuitry may be connected to a digital input of the microcontroller and the microcontroller firmware may be modified to turn off the heating element 240 if the signal indicates that the temperature has exceeded the predetermined level. In one embodiment, this predetermined level may be approximately 300 degree Celsius.

Figure 8:
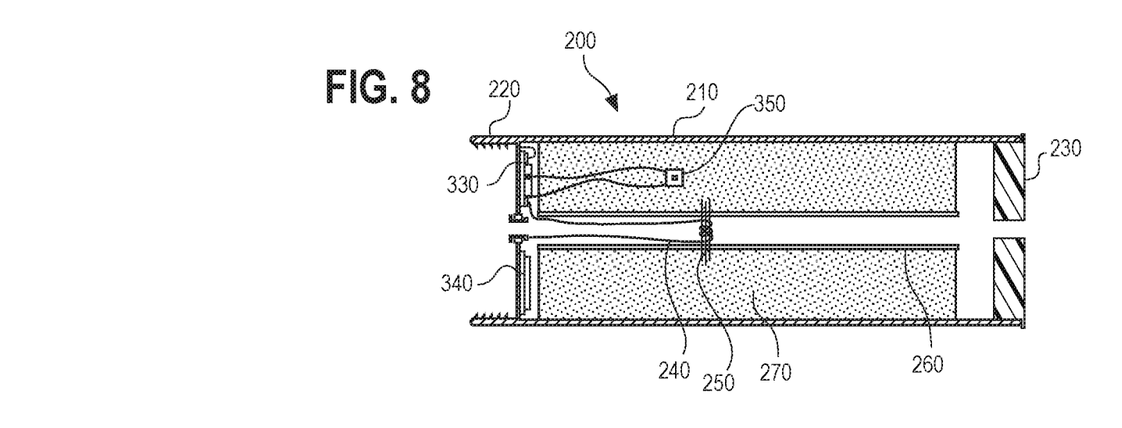
FIG. 8 illustrates another embodiment of a cartomizer of a vaporizer in accordance with the disclosure.

An additional embodiment utilizes a fluid level or humidity sensor 350 with associated circuitry, as illustrated in the cartomizer 200 in FIG. 8. The fluid level sensor 350 (capacitive, resistive or thermal conductivity humidity sensor) may be placed inside the cartomizer 200 in proximity to the heating element 240, inside the fiber batting 270. The associated circuitry may be operable to amplify and determine if the fluid level/humidity is above some predetermined level, as well as a switch 330 (e.g., Power FET) to interrupt the flow of current to the heating coil, may be installed upon a small PCB 340, also contained inside the cartomizer.

Describing certain features of FIG. 8, a heat insulating tube 260 is centrally positioned along a central axis (axis not shown) of the cartomizer. An air flow path (not labeled) is shown within the heat insulating tube 260. Heating element 240 is positioned within the airflow path. Fiber batting 270 surrounds the heat insulating tube 260, forming a hollow cylindrical shape. Fluid level or humidity sensor 350 is embedded within the fiber batting 270. The heat insulating tube 260, the fiber batting 270, and the embedded fluid or humidity sensor 350 are encased in the cartomizer body 210. It should be readily apparent that fluid or humidity sensor 350 (or temperature sensor 320 of FIG. 7) embedded within the fiber batting 270 enables a more compact vaporizer design—without which, the vaporizer would necessarily require increased length or diameter.

Figure 9:
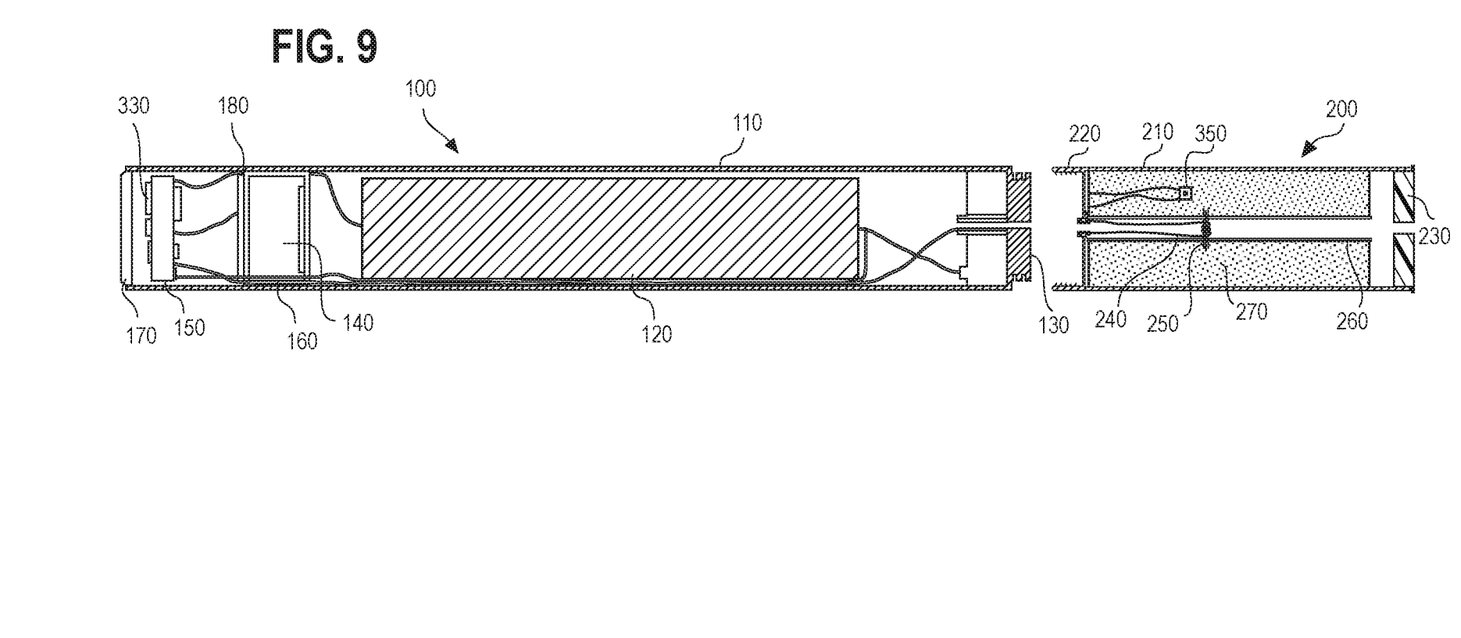
FIG. 9 illustrates an exploded view of another embodiment of a vaporizer including a battery housing and a cartomizer of a vaporizer in accordance with the disclosure.

In another embodiment, referring now to FIG. 9, the associated circuitry and switch 330 may be added to the PCB 150 in the battery housing 100. The output of the associated circuitry may be connected to a digital input of the microcontroller and the microcontroller firmware may be modified to turn off the heating coil if the signal indicates that the fluid level/humidity is below the predetermined level.

Figure 10:
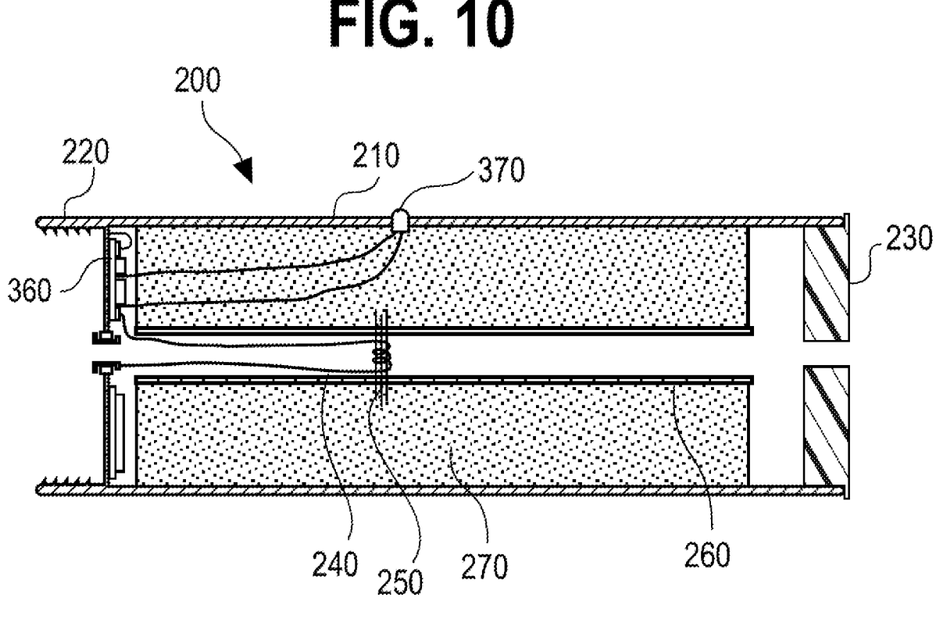
FIG. 10 illustrates another embodiment of a cartomizer of a vaporizer in accordance with the disclosure.

In another embodiment of the disclosure, as illustrated in FIG. 10, a non-volatile memory and counter 360 may be provided on the cartomizer 200 operable to count the number of "puffs" or number of times the cartomizer 200 is activated through user inhalation. This value may be stored in the non-volatile memory so the value is not forgotten in between uses. Once the value reaches some pre-determined maximum value that correlates with the expected life of the vaporizable liquid, the heating element 240 may be disabled through electrical or mechanical means. Optionally, the cartomizer 200 could have an indicator LED 370 or similar flag device to indicate the disabled status to the user.

The non-volatile memory may be read by the microcontroller or dedicated circuitry. The microcontroller may also be configured to activate the optional indicator LED. In some embodiments, this circuitry may be arranged in the cartomizer 200. In other embodiments, this circuitry may be arranged in the battery housing 100. This may require that additional connections between the battery housing 120 and the cartomizer 200. Electrical connections in addition to those operable to activate the heating coil are contemplated within this disclosure. may be added.

Some materials utilized for fiber batting 270 holding the vaporizable fluid begin to dry at approximately 300 degrees Celsius and at a temperature of approximately 600 degrees Celsius the fiber batting may begin to burn, creating an unpleasant and potentially unsafe inhalation experience for the user. Accordingly, embodiments of disclosed herein may permit operation of a vaporizer while preventing unpleasant and potentially unsafe operating temperatures to be reached.

The descriptions set forth above are meant to be illustrative and not limiting, and persons of skill in the art will recognize that various common and known deviations from the above described structures are considered to be within the scope of the disclosed concepts described herein.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

LIST OF REFERENCES 100 battery housing
110 tube
120 battery
130 output connector 140 pressures switch
150 printed circuit board
160 grommet
170 cover
180 insulating plastic
200 cartomizer
210 cartomizer body
220 mating connector
230 mouthpiece
240 heating element
250 fiberglass fibers
260 heat insulating tube
270 fiber batting
310 fusable link
320 temperature sensor
330 switch
340 small PCB
350 fluid level sensor
360 counter
370 LED

What is claimed:

1. A vaporizer comprising:
a battery housing;
a battery housed within the battery housing;
a cartomizer connectable to the battery housing, the cartomizer including
a cartomizer body defining a chamber configured to hold a vaporizable substance, and
a heating element operable to heat the vaporizable substance; and
a cutoff device electrically coupled to the heating element and operable to disrupt a flow of current to the heating element, the cutoff device including a sensor configured to measure a state of the vaporizable substance and output a signal, and the cutoff device further including a fuse configured to separate in order to change or disrupt the flow of current to the heating element, wherein the fuse is indirectly connected to the heating element to prevent tripping during the flow of current to the heating element.

2. The vaporizer of claim 1, wherein the cutoff device includes a switch operable to interrupt the flow of current to the heating element.

3. The vaporizer of claim 1, further comprising an indicator operable to signal a user when the heating element is disrupted.

4. The vaporizer of claim 1, wherein the cutoff device is configured to:
determine, based on the signal, whether the state of the vaporizable substance crosses a predetermined threshold; and
in response to determining that the state of the vaporizable substance crosses the predetermined threshold, interrupt the current flow to the heating element.

5. A vaporizer comprising:
a battery housing;
a battery housed within the battery housing;
a cartomizer connectable to the battery housing, the cartomizer including
a cartomizer body defining a chamber configured to hold a vaporizable substance, and
a heating element operable to heat the vaporizable substance; and
a cutoff device electrically coupled to the heating element and operable to disrupt a flow of current to the heating element, the cutoff device including a sensor configured to measure a state of the vaporizable substance and output a signal, and the cutoff device is configured to disrupt the flow of current to the heating element by modifying the flow of current to the heating element based on the signal, wherein the cutoff device includes a fuse configured to open, wherein the fuse is indirectly connected to the heating element to prevent tripping during the flow of current to the heating element.

6. The vaporizer of claim 5, wherein the cutoff device is configured to:
determine, based on the signal, whether an amount of humidity in the vaporizer crosses a predetermined threshold; and
in response to determining that the amount of humidity in the vaporizer crosses the predetermined threshold, interrupt the current flow to the heating element.

7. The vaporizer of claim 1, wherein the signal is indicative of the state of the vaporizable substance.

8. The vaporizer of claim 1, wherein the cutoff device is configured to permanently decouple the heating element and the battery.

9. The vaporizer of claim 1, wherein the cartomizer further includes a counter configured to count a number of times the cartomizer is activated via user inhalation.

10. The vaporizer of claim 9, wherein the cartomizer further includes a memory configured to store the number of times the cartomizer is activated via user inhalation counted by the counter.

11. The vaporizer of claim 5, wherein the signal is indicative of the state of the vaporizable substance.

12. The vaporizer of claim 5, wherein the cutoff device is configured to permanently decouple the heating element and the battery.

13. The vaporizer of claim 5, wherein the modifying of current flow to the heating element comprises interrupting the current flow.

14. The vaporizer of claim 5, wherein the modifying of current flow to the heating element comprises severing a connection between the heating element and the battery.

15. The vaporizer of claim 5, wherein the cartomizer further includes a counter configured to count a number of times the cartomizer is activated via user inhalation.

16. The vaporizer of claim 15, wherein the cartomizer further includes a memory configured to store the number of times the cartomizer is activated via user inhalation counted by the counter.

17. The vaporizer of claim 1, wherein the sensor is configured to output the signal in response to an exhaustion of the vaporizable substance.

18. A vaporizer comprising:
a battery housing;
a battery housed within the battery housing;
a cartomizer connectable to the battery housing, the cartomizer including
a cartomizer body defining a chamber,
fiber batting disposed within the chamber to hold a vaporizable substance, and
a heating element operable to heat the vaporizable substance; and
a cutoff device electrically coupled to the heating element and operable to disrupt a flow of current to the heating element, wherein:
the cutoff device includes a humidity sensor located inside the fiber batting and configured to output a signal based on the humidity of the chamber, and the cutoff device is configured to disrupt the heating element by interrupting the flow of current to the heating element based on the signal.

19. The vaporizer of claim 18, wherein the cutoff device includes a switch operable to interrupt the flow of current to the heating element.

20. The vaporizer of claim 18, wherein the cartomizer further includes a counter configured to count a number of times the cartomizer is activated via user inhalation.

21. The vaporizer of claim 20, wherein the cartomizer further includes a memory configured to store the number of times the cartomizer is activated via user inhalation counted by the counter.

22. A vaporizer comprising:
   a battery housing;
   a battery housed within the battery housing;
   a cartomizer connectable to the battery housing, the cartomizer including
      a cartomizer body configured to hold a vaporizable substance, and
      a heating element operable to heat the vaporizable substance; and
   a cutoff device electrically coupled to the heating element and operable to disrupt a flow of current to the heating element, the cutoff device including:
      a sensor disposed within the cartomizer body, wherein the sensor is configured to measure a state of the vaporizable substance and output a signal, and
      a switch connectable to the sensor and operable to interrupt the flow of current to the heating element based on the signal.

23. The vaporizer of claim 22, wherein the sensor is a fluid level sensor configured to determine if a fluid level or humidity is above a predetermined level.

24. The vaporizer of claim 22, wherein the cartomizer body includes a fluid reservoir to hold the vaporizable substance, and the sensor is disposed in the fluid reservoir.

* * * * *